United States Patent [19]

Mehra

[11] Patent Number: 5,275,621
[45] Date of Patent: Jan. 4, 1994

[54] METHOD AND APPARATUS FOR TERMINATING TACHYCARDIA

[75] Inventor: Rahul Mehra, Stillwater, Minn.

[73] Assignee: Medtronic, Inc., Minneapolis, Minn.

[21] Appl. No.: 868,048

[22] Filed: Apr. 13, 1992

[51] Int. Cl.$^5$ .............................................. A61N 1/362
[52] U.S. Cl. ...................................................... 607/5
[58] Field of Search ........................................ 128/419

[56] References Cited

U.S. PATENT DOCUMENTS

| | | | |
|---|---|---|---|
| 4,375,817 | 3/1983 | Engle | 128/419 D |
| 4,384,585 | 5/1983 | Zipes | 128/419 D |
| 4,548,209 | 10/1985 | Wielders | 128/419 D |
| 4,559,946 | 12/1985 | Mower | 128/419 D |
| 4,577,633 | 3/1986 | Berkovits | 128/419 PG |
| 4,587,970 | 5/1986 | Holley | 128/419 PG |
| 4,693,253 | 9/1987 | Adams | 128/419 D |
| 4,726,380 | 2/1988 | Vollman | 128/419 PG |
| 4,800,883 | 1/1989 | Winstrom | 128/419 D |
| 4,819,643 | 4/1989 | Menken | 128/419 D |
| 4,830,006 | 5/1989 | Haluska | 128/419.86 |
| 4,880,004 | 11/1989 | Baker | 128/419 PG |
| 4,880,005 | 11/1989 | Pless | 128/419 PG |
| 4,949,719 | 8/1990 | Pless | 128/419 D |
| 4,949,730 | 8/1990 | Pless | 128/419 D |
| 4,953,551 | 9/1990 | Mehra | 128/419 D |
| 5,014,696 | 5/1991 | Mehra | 128/419 D |
| 5,044,374 | 9/1991 | Lindemans | 128/784 |
| 5,163,427 | 11/1992 | Keimel | 128/419 D |

OTHER PUBLICATIONS

Reliable R-Ware Detection from Ambulatory Subjects by Thakor et al Biomedical Science Instrumentation, vol. 4, pp. 67-72, 1978.

Onset and Stability for Ventricular Tachyarrhythmia Detection in an Implantable Pacer-Cardioverter-Defibrillation by Olson et al. in Computers in Cardiology, Oct. 7-10, 1986 pp. 167-170.

Primary Examiner—William E. Kamm
Assistant Examiner—Scott M. Getzow
Attorney, Agent, or Firm—Reed A. Duthler; Harold R. Patton

[57] ABSTRACT

An implantable cardioverter including two electrodes for sensing depolarizations of a chamber of a patient's heart, one electrode providing a near field signal, one electrode providing a far field signal. The device defines a desired cardioversion pulse delivery time as a first time interval following the onset of the far field signal. The device measures a second time interval between the onset of the far field signal and the detection of the near field signal, and delivers the cardioversion pulse synchronized to the detection of the near field signal, using the first and second time intervals to define a synchronization interval following detection of the near field electrogram.

22 Claims, 7 Drawing Sheets

METHOD AND APPARATUS FOR TERMINATING TACHYCARDIA

BACKGROUND OF THE INVENTION

This invention relates to implantable stimulators generally and more particularly to implantable cardioverters and defibrillators.

Cardioversion and defibrillation pulses have traditionally been synchronized to detected cardiac depolarizations. In the context of both external and implantable cardioverters and/or defibrillators, synchronization has been accomplished by means of an R-wave detector, which triggers delivery of a cardioversion or defibrillation pulse a short interval thereafter.

The interval between R-wave detection and delivery of a cardioversion or defibrillation pulse has varied somewhat in different prior art implementations. Most cases the delay appears to be an inherent function of the circuitry of the device, rather than a result of any attempt to produce ideal timing of the defibrillation pulse with respect to the detected R-wave. However, U.S. Pat. No. 4,830,006 issued to Haluska et al. suggests that the delay between R-wave detection from the intracardiac EGM to the delivery of the cardioversion shock should be adjustable by the physician to achieve optimal synchronization.

Traditional R-wave detectors have comprised a bandpass filter and a threshold detector and have generally been used for synchronization purposes. However, synchronization to other features of the electrogram has been proposed. For example, U.S. Pat. No. 4,559,946 issued to Mower suggests synchronization to the point of peak slope of the intracardiac EGM.

As a practical matter, intracardiac or surface R-wave detection circuitry typically detects the occurrence of an R-wave at a point in time which typically occurs somewhat after the onset of the R-wave, and which varies depending upon the morphology of the particular R-wave being sensed. As a result, the synchronization of the cardioversion pulse to the R-wave is somewhat variable. In the context of implantable devices, the R-wave detectors used for synchronization has been coupled to an electrode pair on or in the heart or to an electrode pair comprising a first electrode in or on the heart and a second, remote electrode.

An earlier attempt to provide improved control of the relationship between the depolarization of the heart and the delivery of a cardioversion pulse is set forth in U.S. patent application Ser. No. 07/630,698, for a Paced Cardioversion, filed Dec. 20, 1990, by Mehra, incorporated herein by reference in its entirety. In this application, the inventor proposed overdrive pacing in response to detection of the tachyarrhythmia, and synchronization of the delivered cardioversion pulse to the overdrive pacing pulse. While it is believed that this approach is workable, it does require additional expenditure of energy in the form of overdrive pacing pulses.

SUMMARY OF THE INVENTION

The inventor has determined that precise timing of the delivery of cardioversion pulses in relation to detected R-waves is of substantial importance in order to accomplish cardioversion at a the lowest possible energy level and to minimize the chances of acceleration of the tachycardia. The inventor has determined that to achieve these goals, it is desirable to synchronize the delivery of the cardioversion pulse to the point of onset of the R-wave as measured in a far-field electrogram, delivering the pulse a desired delay ($\Delta$), following the onset. For external devices, the surface electrocardiogram can be used as the far-field electrogram. In the context of an implantable device, the far field electrogram may be obtained by using one or more electrodes located remote from the heart. For example, two more electrodes may be located on the housing of the implantable pulse generator, in a fashion analogous to that disclosed in U.S. patent application Ser. No. 07/681,235 by Combs et al., filed on Apr. 5, 1991, and incorporated herein by reference in it entirety. However, if onset is to be determined by means of digital signal processing, use of the detected onset for synchronization purposes would require that the digital processing necessary in order to determine the time of onset must be completed in a period of time short enough to allow for timing of the synchronization delay, following identification of the point of onset. This approach, while workable, may not be practical in many cases. Therefore, it is proposed that as an alternative, nearfield electrodes, employing a traditional R-wave detector, may be used for synchronization purposes, while preserving the ability to effectively synchronize the defibrillation pulse to the onset of the correspond farfield R-wave.

If rear-field electrodes are used for synchronization purposes, the cardioversion pulse may nonetheless be delivered following an interval ($\Delta$), timed from the onset of an R-wave sensed in a far-field electrogram. The far-field electrogram may be sensed using an electrode in or adjacent the heart and a remote electrode or using two remote electrodes. The time of onset ($T_o$) of a far-field R-wave can be compared to the time of detection ($T_d$) of the corresponding R-wave sensed in a near-field electrogram, using a traditional R-wave detector. The near-field electrogram may be sensed using a pair of closely spaced electrodes located on or in the heart. The time interval ($T_d - T_o = t$) between the two measured points in time can be subtracted from the desired delay interval $\Delta$ to yield a derived delay ($\Delta - t$) which defines an interval before or after near-field R-wave detection which may be used for calculation of the synchronization delay (SD) for the delivered cardioversion pulse which functions equivalently to a delay calculated from the onset of the R-wave taken from the far-field electrodes.

If the derived delay ($\Delta - t$) is positive, synchronization may be from the near-field R-wave detect associated with the R-wave to which delivery of the pulse is to be synchronized. In other words, the cardioversion pulse can be delivered at a synchronization delay $SD = (\Delta - t)$ following the corresponding near-field R-wave detect. However, if the derived delay is negative, synchronization to an R-wave will have to be accomplished by timing from the previous near field R-wave detect. In this case, a near-field R-wave detect will start an augmented synchronization delay period $SD = (VTCL + \Delta - t)$, wherein "VTCL" is the average measured R-R interval of the tachycardia. This will allow delivery of a cardioversion pulse at the desired time following far-field R-wave onset, but timed off the near-field R-wave detect associated with the immediately preceding R-wave.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENTS

Figure 1:
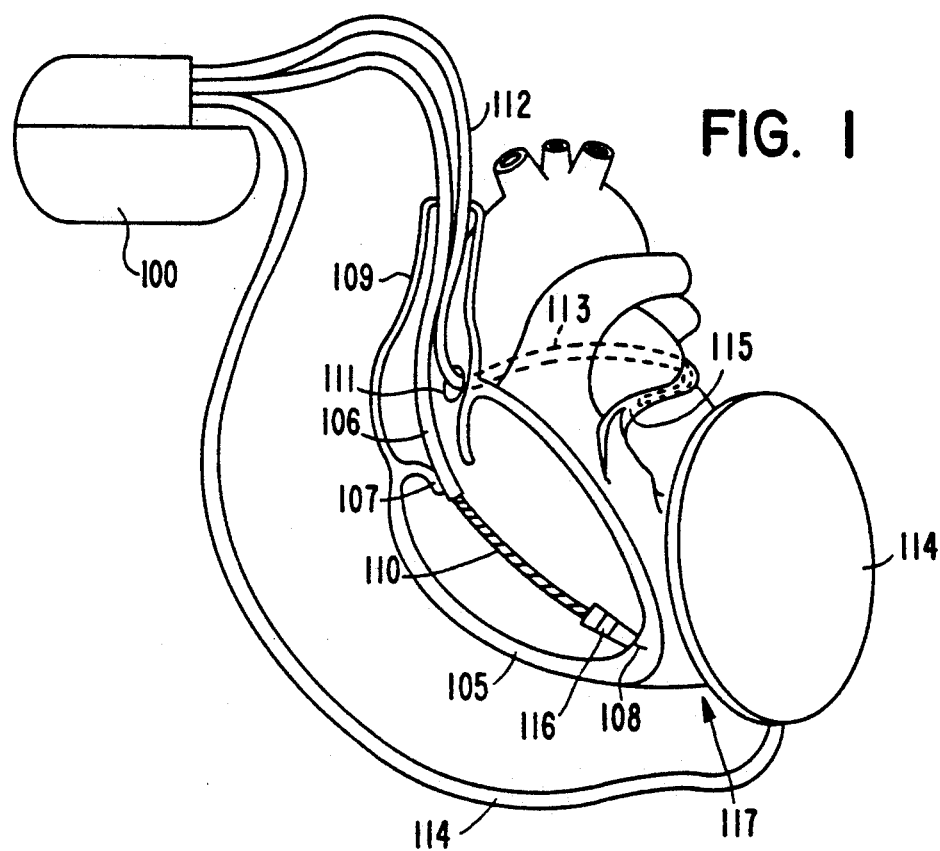
FIG. 1 illustrates a transvenous/subcutaneous electrode system appropriate for use with a pacemaker/cardioverter/defibrillator embodying the present invention.

FIG. 1 illustrates an implantable pacemaker/cardioverter/defibrillator 100 and its associated lead system, as implanted in and adjacent to the heart. As illustrated, the lead system comprises a coronary sinus lead 112, a right ventricular lead 106, and a subcutaneous lead 114. The coronary sinus lead 112 is provided with an elongated electrode located in the coronary sinus 111 and great vein region at 113, extending around the heart until approximately the point 115 at which the great vein turns downward toward the apex of the heart 117. The right ventricular lead 106 includes an elongated defibrillation electrode 110, a ring electrode 116, and helical electrode 108, which is screwed into the tissue of the right ventricle at the right ventricular apex 117. Leads 106 and 112 may correspond to the leads disclosed in U.S. Pat. No. 5,014,696 by Mehra for an "Endocardial Defibrillation Electrode System", issued May 14, 1991 and incorporated herein by reference in its entirety. A subcutaneous electrode lead 114 is also illustrated, implanted in the left chest. Lead 114 may correspond to the lead illustrated in U.S. Pat. No. 5,044,374 by Lindemans et al. for a "Medical Electrical Lead", issued Sep. 3, 1991 and incorporated herein by reference in its entirety.

In conjunction with the present invention, the lead system illustrated provides several electrode pairs which may be employed in the practice of the present invention. The far-field sensing electrode pair may comprise ring electrode 116 paired with an electrode located on the housing of the implantable pulse generator. Electrodes 108 and 116 may be used for near-field sensing. Electrode 116 in conjunction with electrode 108 or in conjunction with an electrode located on the housing of the pulse generator will generally be used for delivery of cardiac pacing pulses. The electrodes on leads 112, 114 and electrode 110 on lead 106 will be used to deliver cardioversion and defibrillation pulses.

Figure 2:
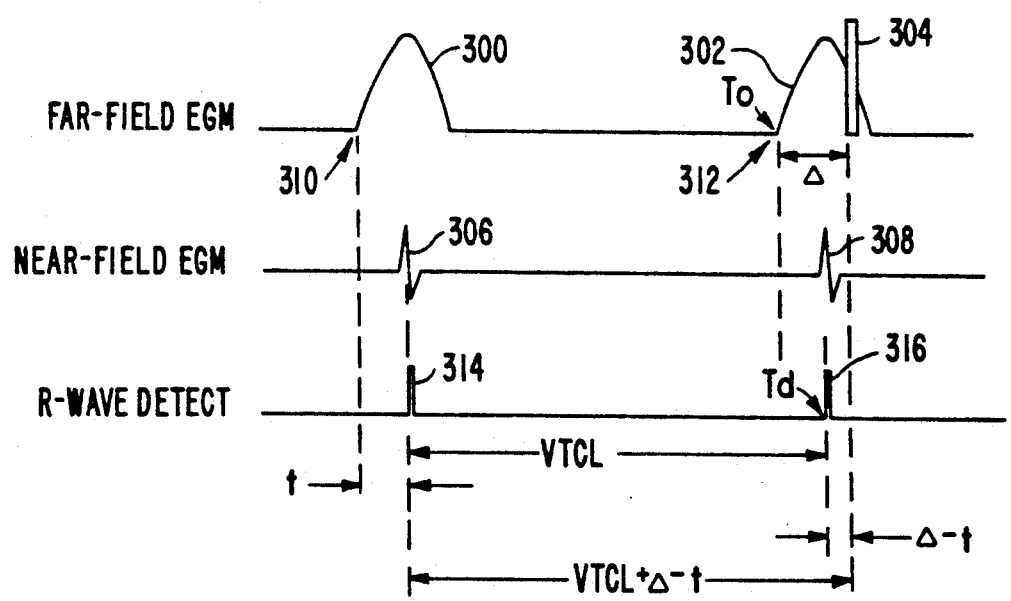
FIG. 2 is a timing chart illustrating the interrelation of the near and far-field electrograms and the time intervals associated therewith for purposes of the present invention.

FIG. 2 illustrates near and far-field electrograms, and the method by which the desired synchronization delay according to the present invention may be derived. The upper tracing illustrates a simulated far-field electrogram, for example as would be taken using electrode 116 (FIG. 1) and a remote electrode. R-waves 300 and 302 are illustrated, along with a synchronized cardioversion pulse 304. The onsets of R-waves 300 and 302, respectively, occur at 310 and 312. The second tracing illustrates a simulated bipolar ventricular electrogram, for example as would be taken between electrodes 108 and 116 (FIG. 1). R-waves 306 and 308 corresponds to R-waves 300 and 302, respectively. The third tracing is an illustration of the output of an R-wave detector, as coupled to the near-field electrode pair used to derive the near-field electrogram of the second tracing. Sense detect signals occur at 314 and 316, corresponding to R-waves 306 and 308, respectively.

As discussed above, the interval "t" is derived by subtracting the point of onset of far-field R-wave 300 from corresponding near-field sense detect 314. The tachycardia cycle length VTCL is illustrated as extending between subsequent R-wave detects 314 and 316. Both methods of calculation of the synchronization delay are illustrated, leading to delivery of the cardioversion pulse 304, a desired delay $\Delta$ after the onset of R-wave 302. In the first instance, the synchronization delay (SD) may be equal to $(\Delta - t)$ and initiated in response to sense detect 316. The result is that the cardioversion pulse 304 is delivered at a point of onset of R-wave 302, plus $\Delta$. The alternative method of calculating the synchronization delay provides a delay calculated from sense detect 314. In this case, the synchronization delay is equal to $(VTCL + \Delta - t)$, and is initiated in response to the sense detect 314 associated with the R-wave 300, preceding the R-wave 302 to which the cardioversion pulse is to be synchronized. In this case the cardioversion pulse 304 is also delivered at the onset of R-wave $302 + \Delta$. The second method of synchronized delay calculation, as discussed above, is believed to be more likely used in those circumstances in which the derived delay $(\Delta - t)$ is negative. However, it may also be used in those instances in which the derived delay is positive, if desired.

For purposes of the present application, the high voltage pulse delivered is referred to as a "cardioversion" pulse. However, it should be kept in mind that in some cases, the early stages of ventricular fibrillation may be difficult to distinguish from a rapid ventricular tachycardia, and in such cases, the delivered cardioversion pulse may actually function as a defibrillation pulse, terminating the early stages of fibrillation. Therefore, for purposes of the invention, the specific nature of the heart rhythm being monitored (tachycardia versus fibrillation) is less important than that ability to reliably sense and synchronize delivery of the high voltage pulse. Therefore, for purposes of the present application, the term "cardioversion" should be construed broadly.

Figure 3:
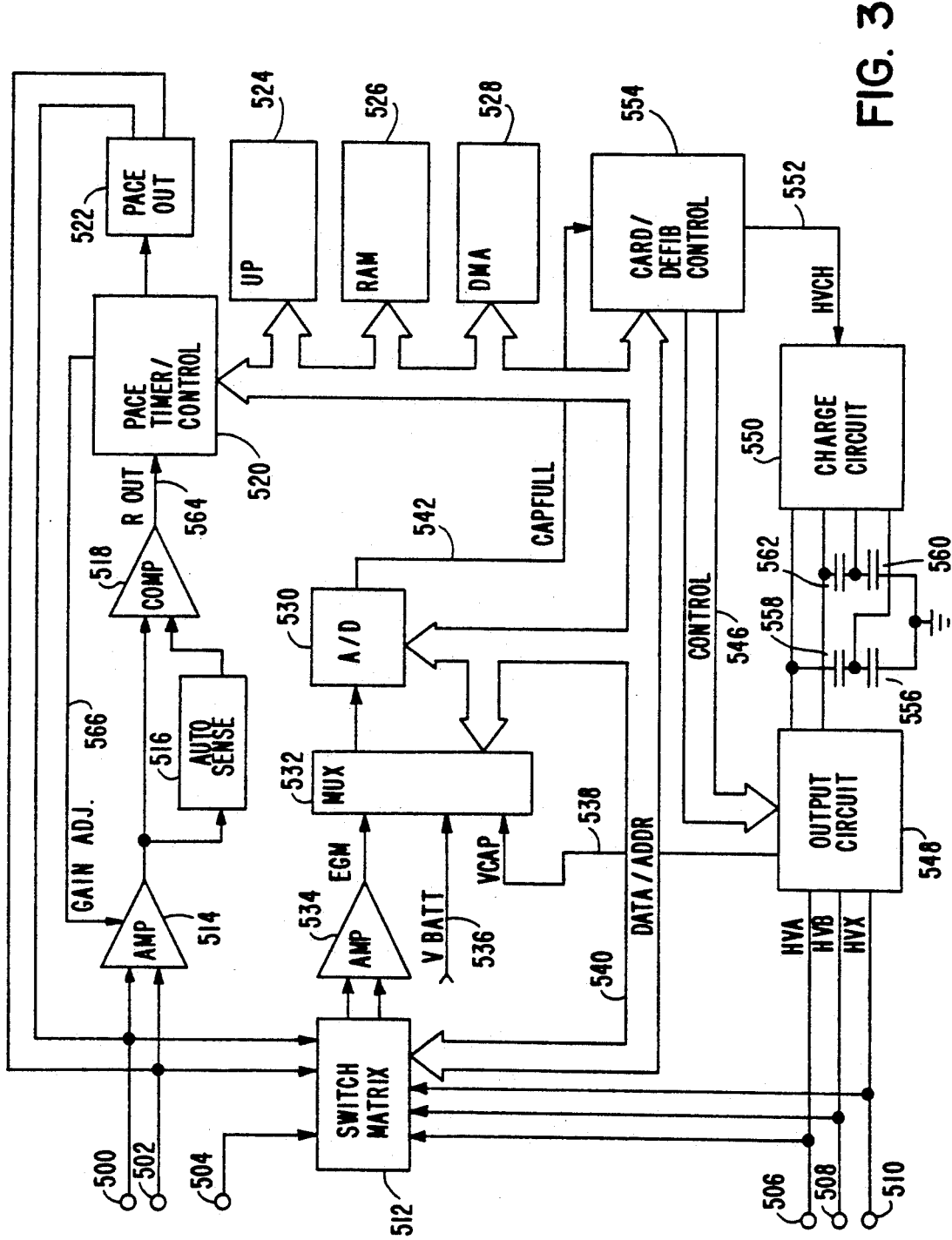
FIG. 3 is a schematic block diagram illustrating the structure of one embodiment of an implantable pacemaker/cardioverter/defibrillator in which the present invention may be embodied.

FIG. 3 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al on Oct. 22, 1985, U.S. Pat. No. 4,693,253, issued to Adams et al on Sep. 15, 1987, U.S. Pat. No. 4,830,006, issued to Haluska et al on May 6, 1989 and U.S. Pat. No. 4,949,730, issued to Pless et al on Aug. 21, 1990, all of which are incorporated herein by reference in their entireties.

The device is illustrated as being provided with six electrodes, 500, 502, 504, 506, 508 and 510. Electrodes 500 and 502 may be a pair of electrodes located in the ventricle, for example, corresponding to electrodes 108 and 116 in FIG. 1. Electrode 504 may correspond to a remote, indifferent electrode located on the housing of the implantable pacemaker/cardioverter/defibrillator.

Electrodes 506, 508 and 510 may correspond to the large surface area defibrillation electrodes located on the ventricular, coronary sinus and subcutaneous leads illustrated in FIG. 1.

Electrodes 500 and 502 are shown as hard-wired to the R-wave detector circuit, comprising bandpass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned, copending U.S. patent application Ser. No. 07/612,760, by Keimel, et al., filed November 15, for an Apparatus for Monitoring Electrical Physiologic Signals, incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al on Nov. 14, 1989, both incorporated herein by reference in their entireties, may also usefully be employed to practice the present invention.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al, published in Biomedical Science Instrumentation, Vol. 4, pp 67-72, 1978, incorporated herein by reference in its entirety.

In the context of the present invention, it is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1-3 seconds following adjustment of the sensing threshold equal to 70-80% of the amplitude of a detected spontaneous R-wave. The invention may also be practiced in conjunction with more traditional R-wave sensors of the type comprising a band pass amplifier and a comparator circuit to determine when the bandpassed signal exceeds a predetermined, fixed sensing threshold.

Switch matrix 512 is used to select which of the available electrodes are to be coupled to sense amp 534, for use in measuring the point of onset of the far-field R-wave. Selection of which electrodes are so employed is controlled by the microprocessor 524 via data/address bus 540. Signals from the selected electrodes are passed through bandpass amplifier 534 and into multiplexer 532, where they are converted to multibit digital signals by A/D converter 530, for storage in random access memory 526 under control of direct memory address circuit 528. Microprocessor 524 analyzes the digitized ECG signal stored in random access memory to identify the points of onset and termination of R-waves sensed between the far-field electrodes.

For example, the microprocessor 524 may analyze the ECG stored in an interval extending from minus 100 milliseconds previous to the occurrence of an R-wave detect signal on line 564, until 100 milliseconds following the occurrence of the R-wave detect signal. The time window thus extends from a time prior to R-wave detection to a point following R-wave detection, and includes a sufficient time (e.g. 200 ms) to assure that the entire R-wave is recorded. After detection of an R-wave and the expiration of the associated time window, the device examines the digital values stored during the time window and determines the width of the R-wave, identifying both the start and end points for the R-wave. The difference between the start and endpoints defines the width of the stored R-wave, which may be used for diagnostic purposes or for classification of arrhythmias. In particular, the width of the R-waves may be used to distinguish sinus tachycardia from ventricular tachycardia.

Copending patent application No. 07/867,931 for a "Method and Apparatus for Discrimination of Ventricular Tachycardia from Supraventricular Tachycardia and for Treatment thereof" by Mader, et al filed on the date of this application discloses a particularly advantageous method of identifying the points of onset and termination of digitized R-waves for use in an implantable device. This application is incorporated herein by reference in its entirety.

In particular, the point of onset may be identified at the point at which a predetermined number of successive digital values exceed the preceding stored digital value by more than a predetermined amount. For example, each digital value may be compared to the most recently stored previous digital value but one, the difference between these two values determined, and their difference compared to a predetermined threshold. If the sign of the difference so calculated remains constant and the difference so calculated remains above a desired threshold for a predetermined number of beats, onset is identified.

For purposes of the present invention, a sampling rate of 256 Hz should be sufficient, although somewhat lower or substantially higher sampling rates may be used, depending on the amount of data storage capacity in RAM 526 and on the processing speed of microprocessor 524. However, any method of identifying the start or onset of a digitized R-wave may usefully be employed in conjunction with the present invention.

The identified point of onset $T_o$ is stored and is compared to the time of occurrence of the near-field R-wave detect $T_d$ signal (on R OUT line 564) which triggered storage of the digitized waveform. The difference "t" between these two times is calculated by microprocessor 524 and stored in memory 526. The desired delay Δ from onset of the far-field R-wave is similarly stored in the memory 526. The value of Δ may be set by the physician by means of an external programmer or may be a function of the rate of the sensed tachyarrhythmia. Generally, it is believed that the optimal value for Δ will be between 80 and 120 ms. The value of t is subtracted from the value of Δ, to produce a derived delay, as discussed above. The functioning of the software used to determine the synchronization delay from these values is discussed in more detail below in conjunction with the flow charts of FIGS. 4, 5 and 6.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of bandpass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including antitachycardia pacing. The duration of the interval defined by the escape interval timer is determined by microprocessor 524, via data/address bus 540. The value of the count present in the escape interval counter when reset by sensed R-waves may be used to measure the duration of R-R intervals, to detect the presence of tachycardia and to determine whether the minimum rate criteria are met for activation of the tachycardia/defibrillation discrimination function.

Microprocessor 524 operates as an interrupt driven device, and responds to interrupts from pacer timing/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an antitachyarrhythmia pacing regimen is desired, appropriate timing intervals for controlling generation of antitachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520, using the selected synchronization delay as discussed above. One embodiment of a system for delivery and synchronization of cardioversion and defibrillation pulses, and controlling the timing functions related to them is disclosed in more detail in copending, commonly assigned U.S. patent application Ser. No. 07/612,761, by Keimel, for an Apparatus for Detecting and Treating a Tachyarrhythmia, filed Nov. 15, 1990 and incorporated herein by reference in its entirety. This basic system, with the addition of the derived synchronization delay provided by the present invention provides a workable implementation of the present invention. However, many known cardioversion or defibrillation pulse generation circuits are believed usable in conjunction with the present invention. For example, it is believed that circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Patent No. 4,375,817, issued to Engle et al, all incorporated herein by reference in their entireties may also be adapted to practice the present invention. Similarly, known circuitry for controlling the timing and generation of antitachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used to in a device for practicing the present invention.

In the illustrated embodiment of the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multielectrode, simultaneous pulse regimen or a multielectrode sequential pulse regimen. Monophasic or biphasic pulses may also be generated. One example of circuitry which may be used to perform this function is set forth in commonly assigned copending patent application Ser. No. 07/612,758, filed by Keimel, for an Apparatus for Delivering Single and Multiple Cardioversion and Defibrillation Pulses, filed Nov. 14, 1990, incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

Figure 4:
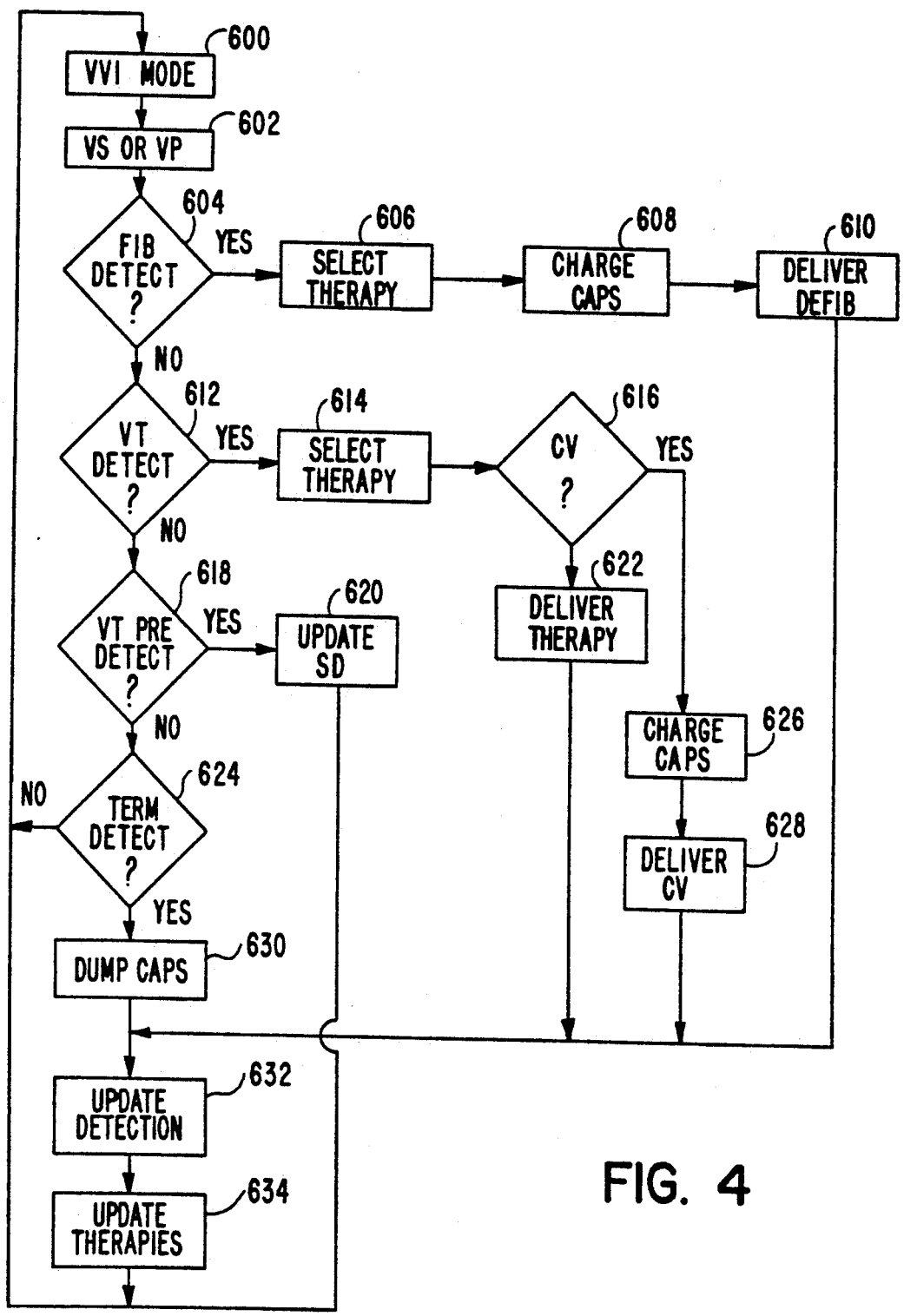
FIGS. 4, 5 and 6 are functional flow charts illustrating the method of operation of the present invention as embodied in a microprocessor based device as illustrated in FIG. 3.
Figure 5:
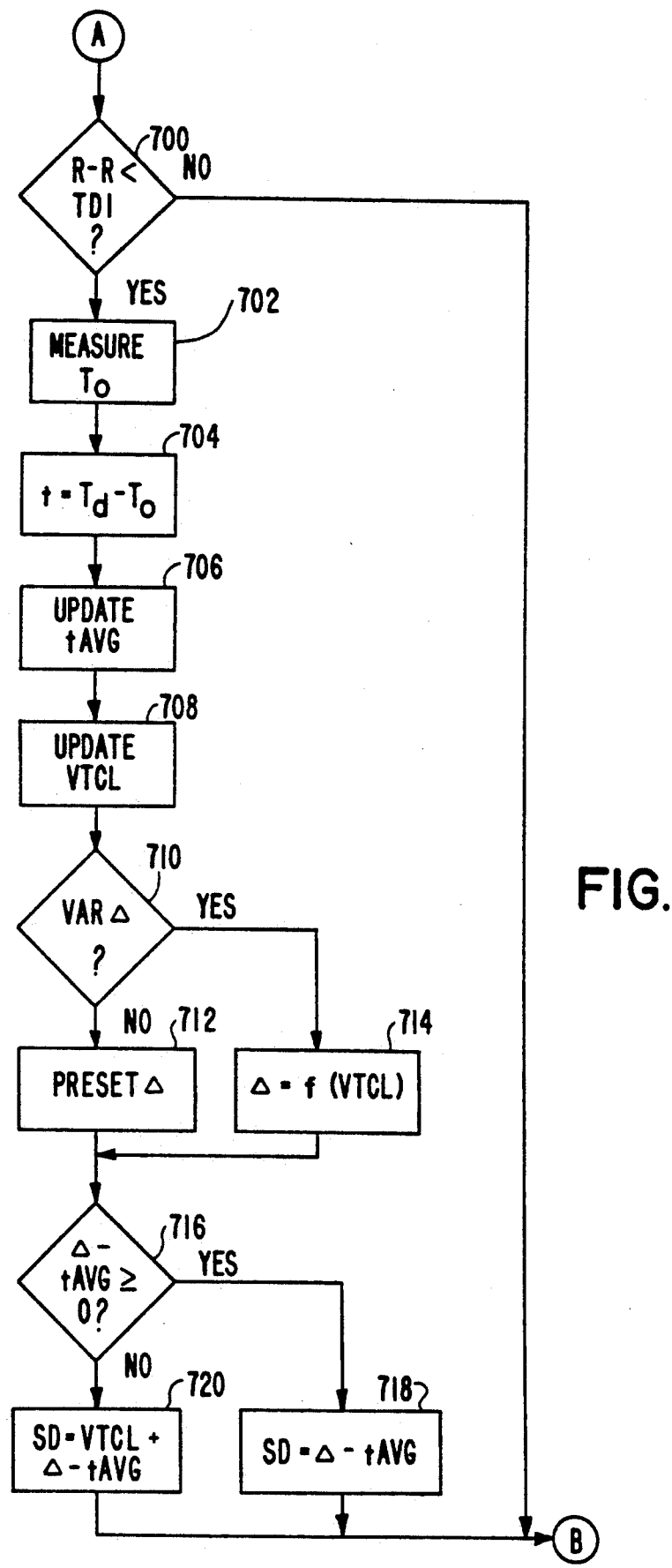
Figure 6:
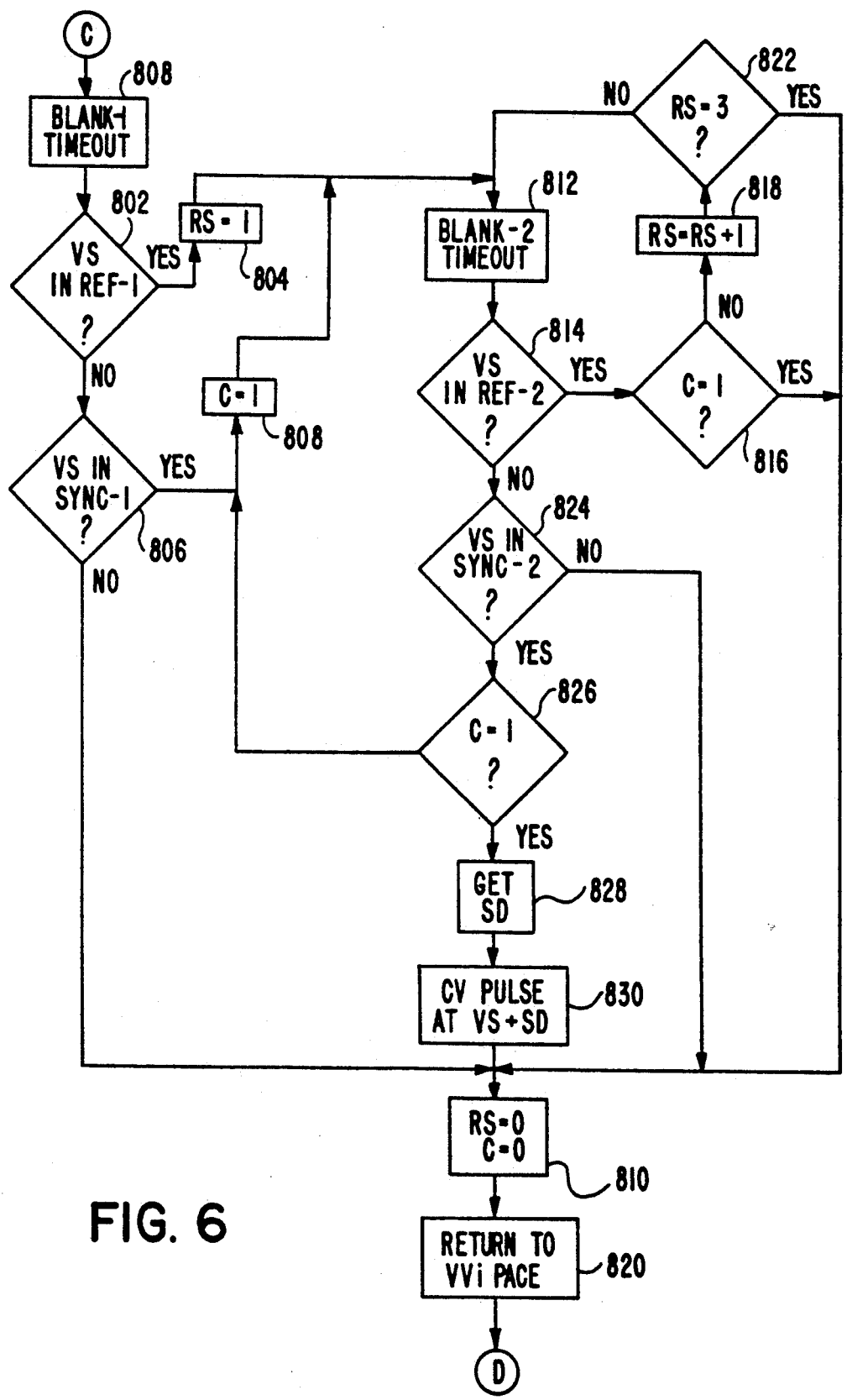

FIGS. 4, 5 and 6 are intended to functionally represent that portion of the software employed by microprocessor 524 (FIG. 3) which is relevant to or implements the synchronization delay. This portion of the software illustrated in FIG. 4 is illustrated functionally and deals with the over-all organization of tachyarrhythmia detection functions during VVI mode pacing, as indicated at 600. The tachyarrhythmia detection functions are activated in response to an interrupt indicative of a sensed or paced beat at 602. In response to this interrupt, the value of the preceding R-R interval, corresponding to the current time on the escape interval counter in pacer timing/control circuitry 520 may be stored at 602 and used as a measurement of the R-R interval for tachyarrhythmia detection functions. In addition, the time of detection ($T_d$) of the sensed ventricular depolarization, as indicated by means of a real time clock within microprocessor 524 is also stored at 602.

Stored information reflective of the previous series of R-R intervals, such as information regarding the rapidity of onset of detected short R-R intervals, the stability of detected R-R intervals, the duration of continued detection of short R-R intervals, the average R-R interval duration and information derived from analysis of stored ECG segments are used to determine whether tachyarrhythmias are present and to distinguish between different types of tachyarrhythmias. Such detection algorithms for recognizing tachycardias are described in the above cited U.S. Pat. No. 4,726,380, issued to Vollmann, U.S. Pat. No. 4,880,005, issued to Pless et al and U.S. Pat. No. 4,830,006, issued to Haluska et al, incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7-10, 1986, IEEE Computer Society Press, 167-170, also incorporated by reference in its entirety herein. However, other criteria may also be measured and employed in conjunction with the present invention.

For purposes of the present invention, the particular details of implementation of the rate and/or R-R interval based VF and VT detection methodologies are not of primary importance. However, it is required the VF and VT rate based detection methodologies employed by the device allow identification and detection of ventricular tachycardia requiring cardioversion. One of the advantages of the present invention is that it is believed practicable in conjunction with virtually any prior art tachycardia detection algorithm.

The microprocessor checks at 604 to determine whether the previous series of R-R intervals are indicative of fibrillation. If so, an appropriate defibrillation therapy is selected at 606, the high voltage capacitors are charged at 608, and a defibrillation pulse is delivered at 610. The above-cited application Ser. No. 07/612,761 by Keimel also discloses a method and apparatus for delivery of synchronized defibrillation pulses. This or other prior systems for delivery of defibrillation pulses may be beneficially be used in the context of the present invention. If fibrillation is not detected at 604, the microprocessor checks at 612 to determine whether the preceding series of detected ventricular depolarizations meet the criteria for detection of tachycardia. If so, a therapy is selected at 614.

In modern implantable antitachyarrhythmia devices, the particular therapies are programmed into the device ahead of time by the physician, and a menu of therapies is typically provided. For example, on initial detection of tachycardia, an antitachycardia pacing therapy may be selected. On redirection of tachycardia, a more aggressive antitachycardia pacing therapy may be scheduled. If repeated attempts at antitachycardia pacing therapies fail, a higher level cardioversion pulse therapy may be selected thereafter. Prior art patents illustrating such pre-set therapy menus of antitachyarrhythmia therapies include the above-cited U.S. Pat. No. 4,830,006, issued to Haluska, et al, U.S. Pat. No. 4,727,380, issued to Vollmann et al and U.S. Pat. No. 4,587,970, issued to Holley et al. The present invention is believed practicable in conjunction with any of the known antitachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In the context of the present invention, it is anticipated that the synchronization delay itself may be varied as function of the scheduled sequence of delivered therapies. For example, with each successive cardioversion attempt, the synchronization delay may be successively increased or decreased. Alternatively, the synchronization delay be increased or decreased as a function of the amplitudes of the scheduled cardioversion pulses.

Figure 7:
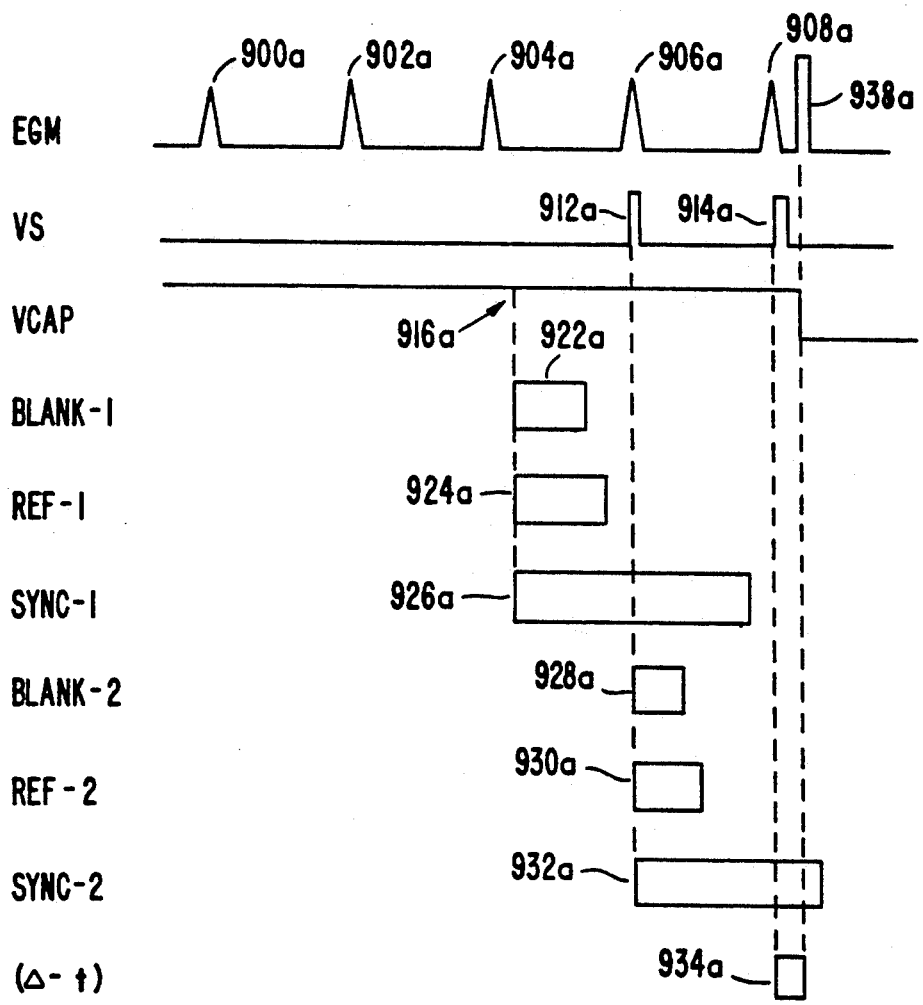
FIGS. 7 and 8 are simulated bipolar endocardial electrograms and associated timing charts illustrating the synchronization of cardioversion pulses using the present invention.
Figure 8:
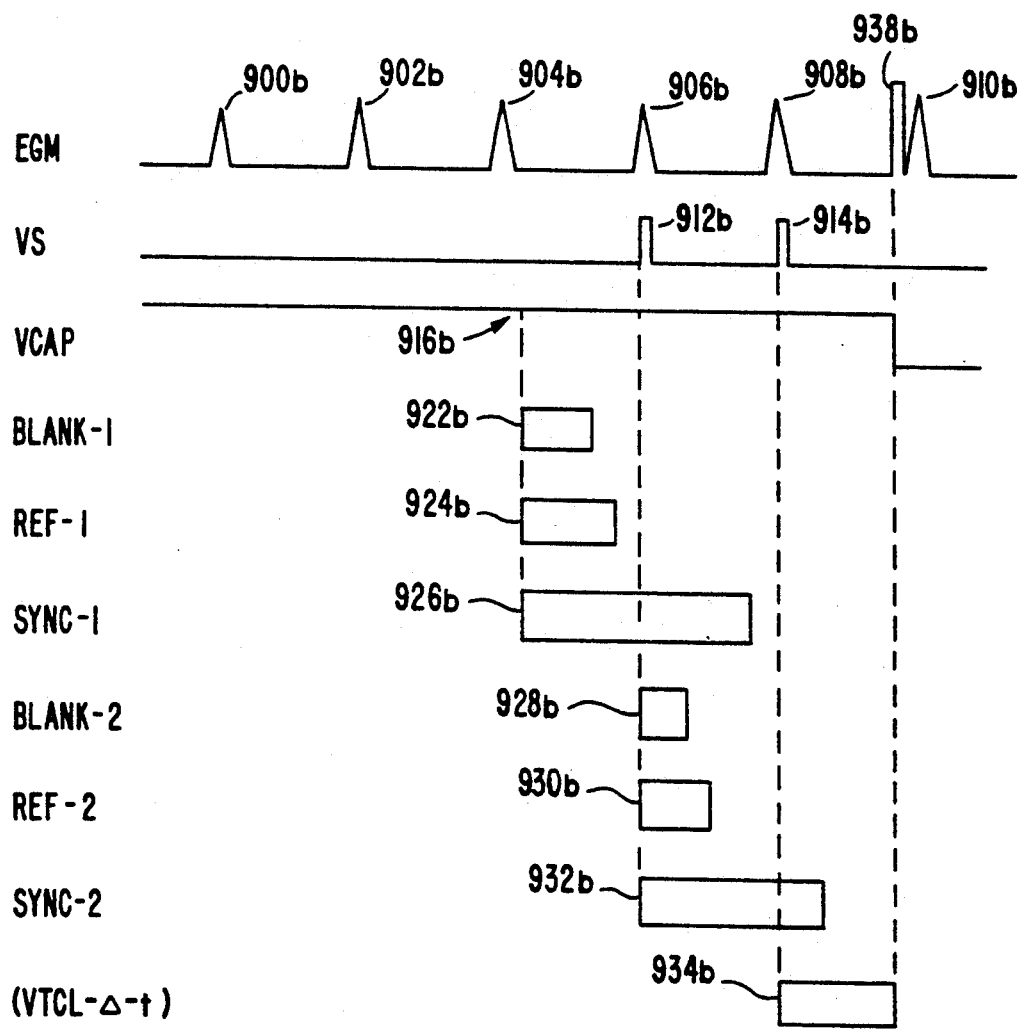

If the selected therapy is a cardioversion pulse, at 616, the high voltage output capacitors are charged at 626, and a cardioversion pulse is delivered at 628, timed from a near-field R-wave detect as described above. FIG. 6, below and FIGS. 7 and 8 illustrate the synchronization of cardioversion pulses to detected R-waves, using the present invention, in some detail. In the event that a therapy other than cardioversion, for example antitachyarrhythmia pacing, is selected, this therapy is similarly delivered at 622. Following delivery of the antitachycardia for defibrillation therapies, detection criteria are updated at 632 to reflect delivery of the previous therapies and the therapy schedule is updated at 634, as described above.

In the present invention, it is desired to calculate the measured interval "t" in the form of a running average value (tAVG), taken over a series of detected R-waves preceding delivery of the cardioversion pulse. As discussed in conjunction with the above-cited Mader application, the pulse width is averaged over a series of approximately 8 beats prior to delivery of antitachycardia therapy. This number of values would appear to be workable in conjunction with the calculation of an average value of tAVG as well. However, it may be that in some cases a greater or lesser number of R-waves are desired in order to calculate tAVG.

In the event that the preceding series of R-waves does not meet the criteria for delivery of an antitachycardia therapy, the microprocessor checks at 616 to determine whether there has been substantial progress toward detection of a tachycardia so that onset measurements may be initiated. Regardless of the detection criteria for triggering delivery of an antitachycardia therapy, it is important that the "predetection" criteria which activates measurement of R-wave onset using the far-field electrodes is defined such that it assures that a significant number of R-waves will be available for measurement, prior to the criteria for delivery of antitachycardia therapies is met. For example, if the criteria for delivery of antitachycardia therapies is a predetermined number of R-waves (NID) having a duration less than a predetermined tachycardia interval (TDI), the measurement of onset of the far-field R-waves can be initiated when the ongoing count of R-waves less than TDI equals NID-X, wherein X is the desired number of values to be employed to calculate tAVG. If the predetection conditions are satisfied, the onset of the stored R-wave is measured and an updated calculation of the synchronization delay (SD) is calculated at 620. The block indicated at 620 corresponds to the functional flowchart illustrated in FIG. 5, which describes the method of calculation of the synchronization delay in more detail.

In the event that the predetection criteria are not met at 618, the microprocessor checks at 624 to determine whether termination of a previously detected tachycardia or a return to normal sinus rhythm during detection of a tachycardia has occurred at 624. As discussed above, this is typically accomplished by sensing a series of R-waves separated by intervals less than the minimum interval for tachycardia detection (e.g., less than VTDI). In the event that termination of previously detected tachycardia or the occurrence of a normal sinus rhythm is recognized at 624, the output capacitors are internally discharged at 630, if they had been previously charged. In the context of delivery of synchronized cardioversion, it is possible that the capacitors may be charged, without the pulse actually being delivered. This again is discussed in more detail in conjunction with the flowchart of FIG. 6. After discharging the output capacitors, the detection criteria is updated at 632 and the therapy menu is updated at 634 to reflect the return to normal sinus rhythm, as discussed above. At this time, it is also envisioned that any stored measurements of t will also be cleared.

FIG. 5 is a functional flowchart illustrating the operation of the functional block 620 in FIG. 4, dedicated to determination of the synchronization delay. At 700, the microprocessor checks to determine whether the preceding R-R interval qualifies as a tachycardia beat. For example, this may be accomplished by comparing the R-R interval to a predetermined interval indicative of a tachycardia, e.g., the TDI interval discussed above. If R-R is less than TDI, measurement of onset is undertaken. If not, the device returns to VVI mode pacing.

At 702, the microprocessor measures the time of onset. As discussed above, this process involves waiting the time out of the measurement window, (e.g. 100 milliseconds after $T_d$), and examining the digitized R-wave to determine the point of onset, as discussed in the above-cited Mader application. At 704, the time of onset $T_o$ is subtracted from the R-wave detection time $T_d$, to yield a value "t". At 706, the running average tAVG of the values of "t" is updated, and at 708 the ventricular cycle length VTCL is updated. This may be a running average of the most recent series of R-R intervals associated with the tachyarrhythmia. For example, it may be the preceding 8 R-R intervals less than TDI. At 710, the microprocessor checks to determine whether the value of $\Delta$ is intended to be fixed, or to vary as a function of the detected tachycardia rate. If the value is preset, it is simply looked up at 712. If the value is intended to be variable, it is calculated at 714 as a function of VTCL. For example, as VTCL decreases, the value of $\Delta$ may decrease from 120 to 80 milliseconds. These values are purely exemplary, and it is believed that the physician will wish to optimize the range of values for $\Delta$ and their correspondence to the value of VTCL, on a patient-by-patient basis.

At 716, the microprocessor checks to determine whether $\Delta - tAVG$ is greater than zero. If not, the synchronization delay is set equal to $VTCL + \Delta - tAVG$. If $\Delta - tAVG$ is greater than or equal to zero, the synchronization delay is set equal to $\Delta - tAVG$ at 718.

FIG. 6 illustrates the functional operation of the tachycardia synchronization method of the present invention. In performing this method, the microprocessor employs timers within pacer circuitry 520 to define synchronization intervals as discussed above. Following detection of ventricular tachycardia and successful charging of the output capacitors, the microprocessor 524 sets the timers in pacer circuitry 520 to define a first synchronization interval SYNC-1, a first refractory interval REF-1 and a first blanking interval BLANK-1. During time out of BLANK-1 at 800, ventricular sensing is disabled. In response to an interrupt indicating ventricular sensing during REF-1 at 802, the microprocessor 524 notes the occurrence of the refractory sense at 804, and initiates timing of a second synchronization interval SYNC-2, a second refractory interval REF-2 and a second blanking interval BLANK-2.

In the event that no interrupt indicating the occurrence of ventricular sensing occurs during REF-1, the microprocessor continues to wait for the occurrence of an interrupt indicating ventricular sensing during SYNC-1. If an interrupt occurs at 806, the microprocessor notes it at 808, and initiates SYNC-2, REF-2 and BLANK-2, as discussed above. In the absence of sensed events occurring during SYNC-1, the microprocessor resets any internal flags set at 810, and returns the function of the device to the programmed bradycardia pacing mode at 820.

In the event that a second synchronization interval is initiated, after expiration of BLANK-2 at 812, the microprocessor waits for an interrupt during REF-2 indicative of ventricular sensing. If such an interrupt occurs at 814, the microprocessor checks at 816 to determine whether an internal flag (C=1) has been set at 816 indicative of previous sensing during the post-refractory portion of SYNC-1. If this flag has been set, microprocessor returns the operation of the device directly to the programmed VVI brady pacing mode at 820. If the flag has not been set at 816, the microprocessor increments the count (RS) of sensed events occurring during refractory periods at 818, and checks to see whether three successive refractory sense events have occurred at 822. In the presence of three refractory sense events (that is, R-wave interrupts occurring during the refractory intervals of three successive synchronization intervals) the microprocessor directly returns the operation of the device to the programmed VVI bradycardia pacing mode at 820.

Assuming that the occurrence of three successive R-wave interrupts during refractory intervals has not occurred, microprocessor 524 initiates timing of a third synchronization interval, having the same parameters as the second synchronization interval. In the event that no R-waves are sensed during REF-2, the microprocessor continues to wait at 824, for an interrupt indicating the occurrence of an R-wave during the post-refractory portion of SYNC-2. In the event that no such R-wave is sensed, the microprocessor resets all internal flags at 810, and reinitiates VVI bradycardia pacing.

In the event that the microprocessor receives an interrupt indicating the occurrence of an R-wave during SYNC-2 at 824, the microprocessor checks at 826 to determine whether a previous R-wave has been sensed in the post-refractory portion of a synchronization interval at 826. If an R-wave previously has been sensed in the post-refractory portion of a previous synchronization interval, at 828 the microprocessor reads the value of the synchronization delay SD previously calculated and at 830 initiates delivery of a cardioversion pulse timed from the most recent R-wave interrupt. Microprocessor 526 then resets all internal flags at 810, and then returns to programmed VVI bradycardia pacing at 820.

In the event that an R-wave is sensed during the post-refractory portion of SYNC-2 at 824, but there is no internal flag set indicating the occurrence of a previous post-refractory sensed R-wave at 826, the microprocessor sets a flag indicating R-wave sensing in the post refractory portion at 808 and initiates timing of the third synchronization interval, employing the same time parameters as the second synchronization interval.

The microprocessor 526 continues to define synchronization intervals having the time parameters of the second synchronization interval until either one of the synchronization intervals expires without ventricular sensing, three R-waves occur within refractory intervals within synchronization intervals, or two R-waves are sensed during the non-refractory portions of successive synchronization intervals. As a practical matter, given the method as illustrated in FIG. 6, a maximum of four synchronization intervals may be required, in some cases. However, in most cases two or three synchronization intervals will be adequate in order to determine whether a synchronous cardioversion pulse is delivered.

FIG. 7 shows a simulated near-field EGM strip, evidencing a ventricular tachycardia indicated by closely spaced R-waves 900a, 902a, 904a, 906a and 908a. FIG. 7 illustrates the operation of the invention to synchronize delivery of cardioversion pulses in the case where the synchronization delay is initiated in response to the near-field R-wave detect corresponding to the R-wave to which the pulse is synchronized. In other words, this figure illustrates the case in which the synchronization delay $SD = (\Delta - tAVG)$.

It is assumed that microprocessor 526 has already detected the occurrence of this tachyarrhythmia, and has enabled the high voltage charging circuitry to initiate charging of the output capacitors. At point 916, the voltage on VCAP line 538 (FIG. 1) reaches the programmed voltage, terminating the charging process. Following the charging process, an initial blanking interval BLANK-1, 922a, is defined. An appropriate duration for this blanking interval can be 300 ms. An initial refractory interval REF-1, 924a, is also defined. An appropriate duration for this interval may be 400 ms.

An initial synchronization interval SYNC-1, 926a, is also defined. The duration of this interval is preferably a function of the rate criterion for tachycardia detection. In particular, it is recommended that this interval be equal to the tachycardia detection interval (TDI) plus a predetermined time increment, for example 360 ms.

R-wave 906a occurs during the post-refractory portion of the first synchronization interval 926a, and initiates the second synchronization interval 932a. A second blanking interval BLANK-2, 928a, is also initiated. This interval may be, for example, 120 ms., and may correspond to the blanking interval used following ventricular sensing during brady pacing or may be a separately defined value. Also initiated is a second refractory interval REF-2, 930a, which may be, for example, 200 ms., and again may correspond either to the normal refractory interval employed by the device following sensed ventricular contractions, or may be separately defined.

The second synchronization interval SYNC-2, 932a, is preferably also a function of the tachycardia detection rate criterion as discussed above, and may be, for example, the tachycardia detection interval (TDI) plus 60 ms. Because R-wave 908a is the second successive R-wave sensed within the post-refractory portion of a synchronization interval, it initiates timing of the synchronization delay SD, 934a, and triggers delivery of a cardioversion pulse at 938a on its expiration. Following generation of the cardioversion pulse at 938a, the device returns to VVI bradycardia pacing.

It should be noted that following delivery of the cardioversion pulse at 938a, some voltage may remain on the output capacitors. This voltage will not be discharged until detection of VT termination. As discussed above, microprocessor 526 may detect VT termination in response the occurrence of a predetermined number of sequential R-R intervals greater than the tachycardia detection interval. Following detection of termination, the output capacitors may be discharged internally as discussed above.

FIG. 8 illustrates the operation of the invention to synchronize delivery of cardioversion pulses in the case where the synchronization delay is initiated in response to the near-field R-wave detect corresponding to the R-wave previous to the R-wave to which the pulse is synchronized. In other words, this figure illustrates the case in which the synchronization delay equals $(VTCL + \Delta - t)$. All numbered elements of FIG. 8 correspond to similarly numbered elements of FIG. 7, with only one difference. All steps leading to delivery of the cardioversion pulse correspond exactly to those correspondingly numbered in FIG. 7, but in this case, the synchronization delay SD is calculated to result in synchronization of the pulse 938b with R-wave 910b, rather than R-wave 908b.

It should be recognized that although the disclosed embodiment deals with fibrillation and tachycardia in the lower chambers or ventricles of the heart, the invention may be usefully practiced in the context of the upper chambers or atria of the heart, which are also prone to tachycardia and fibrillation in some patients. Similarly, it should be understood that the present invention, while particularly adapted for use in or in conjunction with an implantable cardioverter/defibrillator may also be usefully practiced in conjunction with an external cardioverter. It is believed that synchronization based on the point of onset of the far-field EGM is of value in this context as well.

In conjunction with above application, we claim:
1. An implantable cardioverter, comprising:

first electrode means for sensing signals from a chamber of a heart indicative of depolarizations of said chamber of said heart;

second electrode means for sensing signals from said chamber of said heart indicative of depolarizations of said chamber of said heart;

first detecting means coupled to said first electrode means for detecting the occurrence of a first event within a said signal from said chamber of said heart indicative of a depolarization of said chamber of said heart;

second detecting means coupled to said second electrode means for detecting the occurrence of a second event within a said signal from said chamber of said heart indicative of a depolarization of said chamber of said heart;

means for measuring a time differential between the occurrences of said first and second events;

means for defining a cardioversion pulse delay as a function of said measured time differential;

means for initiating timing of a said cardioversion pulse delay upon the occurrence of a said second event; and means for delivering a cardioversion pulse to said heart upon the expiration of a said cardioversion pulse delay.

2. A cardioverter according to claim 1 further comprising an electrical lead, wherein said second electrode comprises an electrode mounted to said lead.

3. A cardioverter according to claim 1 or claim 2 further comprising a housing, wherein said first electrode means comprises at least one electrode mounted to said housing.

4. A cardioverter according to claim 1 wherein said first event comprises the point of onset of a said signal from said chamber of said heat indicative of a depolarization of said chamber of said heart;

5. A cardioverter according to claim 1 or claim 4 wherein said second event comprises the point at which said signal from said chamber of said heart indicative of a depolarization of said chamber of said heart exceeds a predetermined amplitude;

6. A cardioverter according to claim 5 further comprising a housing, wherein said first electrode means comprises at least one electrode mounted to said housing.

7. A cardioverter according to claim 5 further comprising a electrical lead, wherein said second electrode means comprises at least a first electrode mounted adjacent a distal end of said lead.

8. A cardioverter according to claim 7 wherein said first electrode means comprises a second electrode mounted to said lead, spaced from and proximal to said first electrode.

9. A cardioverter according to claim 1 wherein said defining means comprises means for modifying said measured time differential by a predetermined amount to define said cardioversion pulse delay.

10. A method of cardioversion, comprising:
employing a first electrode means for sensing signals from a chamber of a heart indicative of depolarizations of said chamber of said heart;
employing a second electrode means for sensing signals from said chamber of said heart indicative of depolarizations of said chamber of said heart;
detecting the occurrence of a first event within a said signal from said first electrode means indicative of a depolarization of said chamber of said heart;
detecting the occurrence of a second event within a signal from said second electrode means indicative of a depolarization of said chamber of said heart;
measuring a time differential between the occurrences of said first and second events;
defining a cardioversion pulse delay as a function of said measured time differential;
initiating timing of a said cardioversion pulse delay upon the occurrence of a said second event; and
delivering a cardioversion pulse to said heart upon the expiration of a said cardioversion pulse delay.

11. A method according to claim 10 wherein said step of employing said second electrode means comprises locating an electrode within said chamber of said heart.

12. A method according to claim 10 or claim 11 wherein said step of employing said first electrode means comprise locating at least one electrode outside of said chamber of said heart.

13. A method according to claim 10 wherein step of detecting said first event comprises detecting the point of onset of a said signal from said chamber of said heart indicative of a depolarization of said chamber of said heart;

14. A method according to claim 10 or claim 13 wherein said step of detecting said second event comprises detecting the point at which said signal rom said chamber of said heart indicative of a depolarization of said chamber of said heart exceeds a predetermined amplitude;

15. A method according to claim 14 wherein said step of employing said first electrode means comprises locating at least one electrode subcutaneously.

16. A method according to claim 14 wherein said second electrode means comprises at least a first electrode located adjacent a distal end of an electrode lead and wherein said step of employing said second electrode means comprises locating said first electrode within said chamber of said heart.

17. A method according to claim 16 wherein said first electrode means comprises a second electrode mounted to said lead, spaced from and proximal to said first electrode.

18. A method according to claim 14 wherein said second electrode means comprises at least a first electrode located adjacent a distal end of an electrode lead and wherein said step of employing said second electrode means comprises locating said first electrode on said chamber of said heart.

19. A method according to claim 10 wherein said step of employing said second electrode means comprises locating an electrode on said chamber of said heart.

20. A method according to claim 10 wherein said step of defining comprises modifying said measured time differential by a predetermined amount to define said cardioversion pulse delay.

21. A cardioverter, comprising:
means for sensing far-field signals indicative of the depolarizations of a chamber of a heart;
means for measuring the point of onset of a said far-field signal;
means for detecting near-field signals indicative of depolarizations of said chamber of said heart;
means for measuring a time differential between the point of onset of a said far-field signal and the detection of a said near-field signal and for defining a delay interval as a function thereof;
means for initiating said delay interval in response to detection of a said near field signal; and means for generating a cardioversion pulse on expiration of said delay interval.

22. A method of cardioverting a heart, comprising:
sensing far-field signals indicative of the depolarizations of a chamber of a heart;
measuring the point of onset of a said far-field signal;
detecting near-field signals indicative of depolarizations of said chamber of said heart;
measuring a time differential between the point of onset of a said far-field signal and the detection of a said near-field signal and defining a delay interval as a function thereof;
initiating said delay interval in response to detection of a said near field signal and;
generating a cardioversion pulse on expiration of said delay interval.

* * * * *